United States Patent
Wan

(10) Patent No.: US 11,786,238 B2
(45) Date of Patent: Oct. 17, 2023

(54) SURGICAL INSTRUMENTS

(71) Applicant: Genesis Medtech (USA) Inc., Saint Louis Park, MN (US)

(72) Inventor: Shan Wan, Plymouth, MN (US)

(73) Assignee: GENESIS MEDTECH (USA) INC., Saint Louis Park, MN (US)

(*) Notice: Subject to any disclaimer, the term of this patent is extended or adjusted under 35 U.S.C. 154(b) by 0 days.

(21) Appl. No.: 18/085,786

(22) Filed: Dec. 21, 2022

(65) Prior Publication Data
US 2023/0200810 A1 Jun. 29, 2023

Related U.S. Application Data

(60) Provisional application No. 63/293,640, filed on Dec. 23, 2021.

(51) Int. Cl.
| | |
|---|---|
| *A61B 17/068* | (2006.01) |
| *A61B 17/32* | (2006.01) |
| *A61B 17/072* | (2006.01) |
| *A61B 17/00* | (2006.01) |

(52) U.S. Cl.
CPC .. *A61B 17/0684* (2013.01); *A61B 17/320068* (2013.01); *A61B 2017/00849* (2013.01); *A61B 2017/00858* (2013.01); *A61B 2017/07285* (2013.01); *A61B 2017/320074* (2017.08); *A61B 2017/320078* (2017.08); *A61B 2017/320089* (2017.08); *A61B 2017/320093* (2017.08)

(58) Field of Classification Search
CPC .......... A61B 17/320092; A61B 2017/320074; A61B 2017/320093; A61B 2017/320094; A61B 2017/320078; A61B 2017/320089; A61B 2017/00858
See application file for complete search history.

(56) References Cited

U.S. PATENT DOCUMENTS

| | | | |
|---|---|---|---|
| 7,059,509 B2 | 6/2006 | Brown | |
| 10,758,231 B2 | 9/2020 | Harris et al. | |
| 2009/0030311 A1* | 1/2009 | Stulen | A61B 17/320092 600/439 |
| 2009/0143806 A1* | 6/2009 | Witt | A61L 31/08 427/2.28 |

(Continued)

OTHER PUBLICATIONS

International Application No. PCT/US 22/53599 International Search Report and Written Opinion dated May 25, 2023, 13 pages.

*Primary Examiner* — Ashley L Fishback
(74) *Attorney, Agent, or Firm* — MagStone Law, LLP; Enshan Hong

(57) ABSTRACT

The present invention discloses a surgical stapler instrument. The surgical stapler instrument comprises a handle assembly having a proximal end and a distal end. A bottom jaw is detachably coupled to the distal end of the handle assembly. The bottom jaw having a staple cartridge surface, configured to eject one or more staples. Further, a top jaw is detachably coupled to the bottom jaw toward the distal end of the handle assembly. The top jaw comprises a staple pocket disposed over an anvil surface of the top jaw and configured to bend the ejected one or more staples and deliver into targeted tissues. An effective friction coefficient ($\mu e$) of the staple pocket of the top jaw is lower than the staple cartridge surface of the bottom jaw to achieve optimized stapling.

6 Claims, 8 Drawing Sheets

(56) References Cited

U.S. PATENT DOCUMENTS

2011/0196399 A1\* 8/2011 Robertson ...... A61B 17/320783
   606/169
2015/0297235 A1 10/2015 Harris et al.
2019/0175173 A1 6/2019 Harris et al.
2022/0031313 A1 2/2022 Bakos et al.
2022/0395272 A1 12/2022 Fox \* cited by examiner

SURGICAL INSTRUMENTS

FIELD OF THE DISCLOSURE

The present invention generally relates to a surgical shear instrument, and more particularly relates to a surgical instrument configured for cutting, dressing, sealing, and stapling soft tissue.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Mechanical tools have been used in a variety of open surgical procedures for centuries. Such mechanical tools became the natural extension of surgeons' hand to perform a specific function for treating diseased tissue and organs. Typically, there are different types of surgical procedures that are commonly conducted including laparoscopy, endoscopy, arthroscopy, bronchoscopy, gastroscopy etc. Laparoscopy or laparoscopic procedures are used commonly since it is a minimal invasive solution for a wide spectrum of procedures such as cholecystectomy, appendectomy, hernia, and other more complex general/colorectal/GYN/bariatric procedures. Further, extensive improvement in the mechanical tools have been made to support surgeons' job to perform surgical cutting, dissection, coagulation, tissue manipulation and management. Therefore, energy driven devices, such as advanced radio frequency (RF) bipolar, and ultrasonic scalpel system, have gain popularity due to this improvement. During surgery, such energy driven devices may be used to precisely cut or staple tissue from the inside or outside of the human body. Moreover, a secure compression is essential for good tissue effects intra-operatively and tissue healing post-operatively, especially for stapling and energy devices like ultrasonic shear or bi-polar RF shear.

Further, mechanical compression and/or energy inputs have often been used both in open and laparoscopic devices to induce tissue effects. To get the best results from a stapler and a good seal from an energy device, tissue compression is essential. Tissue flow and motion are influenced by compression force, tissue properties, and tissue/device interface interaction during the compression stage. Further, the energy tools such as, ultrasonic blades and—bi-polar jaw surfaces are optimized to maintain a smooth tissue flow and motion. Moreover, the certain surgical staplers as disclosed in U.S. Pat. No. 7,059,509B2, U.S. Ser. No. 10/758,231B2 have been provided with an improved tissue flow control mechanism on one side of stapling jaw, i.e., the plastic cartridge for enhanced gripping and manipulation of tissue.

However, for surgical shears or staplers with opposing jaws, none of these attempts consider the influence of differential friction on an opposite surface of the targeted tissue. It is usual for the opposing jaws to be composed of different materials and to have a varied surface roughness. Typically, normal surgical stapler jaws, for instance, comprise of anvils made of stainless steel and a cartridge surface made of plastic. It is also known that the friction coefficient between tissues and stainless steel differs greatly from the friction between plastic and tissues. Similarly, the ultrasonic shear jaws are composed of a titanium blade and a Teflon jaw surface. Due to the differential friction between the opposing jaws, the tissue adjacent to the two jaw surfaces may flow differently during the tissue compression and manipulation and thus results in non-uniform tissue deformation, which can generate a lateral shear force due to the non-uniform flow. Due to the non-parallel closure of the jaw, this lateral force is amplified. Further, inconsistent compression and lateral force may therefore result in suboptimal staple generation for staplers and inferior sealing performance for the energy driven devices.

Given the aforementioned variations in the prior art, there is a need for the creation of surgical tools with optimum tissue compression, like ultrasonic shear, RF shear device, and surgical stapler, with improved interaction surface friction for better tissue compression and control.

SUMMARY OF THE INVENTION

According to one aspect, a surgical stapler instrument is disclosed. The surgical stapler instrument comprises a handle assembly having a proximal end and distal end. Further, a bottom jaw is detachably coupled to the distal end of the handle assembly. The bottom jaw is having a staple cartridge surface configured to eject one or more staples. Further, a top jaw is detachably coupled to the bottom jaw towards the distal end of the handle assembly. The top jaw comprises a staple pocket disposed over an anvil surface of the top jaw. The anvil surface of the top jaw is configured to bend the ejected one or more staples and deliver into targeted tissues. Further, an effective friction coefficient ($\mu e$) of the staple pocket of the top jaw is lower than the staple cartridge surface of the bottom jaw to achieve optimized stapling.

In one embodiment, delta of the effective friction coefficient ($\Delta \mu e$) for the top jaw and the bottom jaw is less than or equal to 0.25, to control lateral force. It can be noted that the delta of the effective friction coefficient ($\Delta \mu e$) corresponds to a change in friction coefficient between the top jaw and the bottom jaw. In one embodiment, the staple cartridge surface has higher effective friction coefficient ($\mu e$) as compared to the anvil surface, to achieve low friction force.

According to another aspect, a surface optimized surgical shear instrument is disclosed. The surgical shear instrument comprises a handle assembly having a proximal end and a distal end. Further, an ultrasonic blade is detachably coupled to the distal end of the handle assembly and a non-active jaw is detachably coupled to the ultrasonic blade towards the distal end of the handle assembly. The ultrasonic blade is configured to vibrate at high frequency with an effective friction coefficient varying from a distal tip section to a proximal node section. It can be noted that the distal tip section corresponds to a leading section and the proximal node section corresponds to a trailing section of the ultrasonic blade. In one embodiment, a change in surface friction coefficient along a length of the ultrasonic blade, between the distal tip section and the proximal node section, is greater or equal to 0.1. It can be noted that the change in the surface friction coefficient along the length of the ultrasonic blade is achieved by a surface treatment between the distal tip section and the proximal node section.

In one embodiment, the ultrasonic blade having a top surface and a bottom surface. The effective friction coefficient ($\mu e$) of the top surface is greater than the effective friction coefficient ($\mu e$) of the bottom surface to retain a tissue and vessel during a surgery. In one embodiment, the effective friction coefficient (μe) of the top surface and the bottom surface is reversible in case of executing blade back cutting operation.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Some embodiments of this disclosure, illustrating all its features, will now be discussed in detail. The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The present invention discloses a surgical stapler with two opposing jaws with an effective coefficient of friction difference and the resulted lateral force applied onto on the two opposing jaws of the surgical stapler is optimized for a compressed tissue when delta of two coefficients is less than 0.25. Further, the surfaces of the two opposing jaws are treated with uniform surface friction from the jaw tip to the end of jaw.

Figure 1:
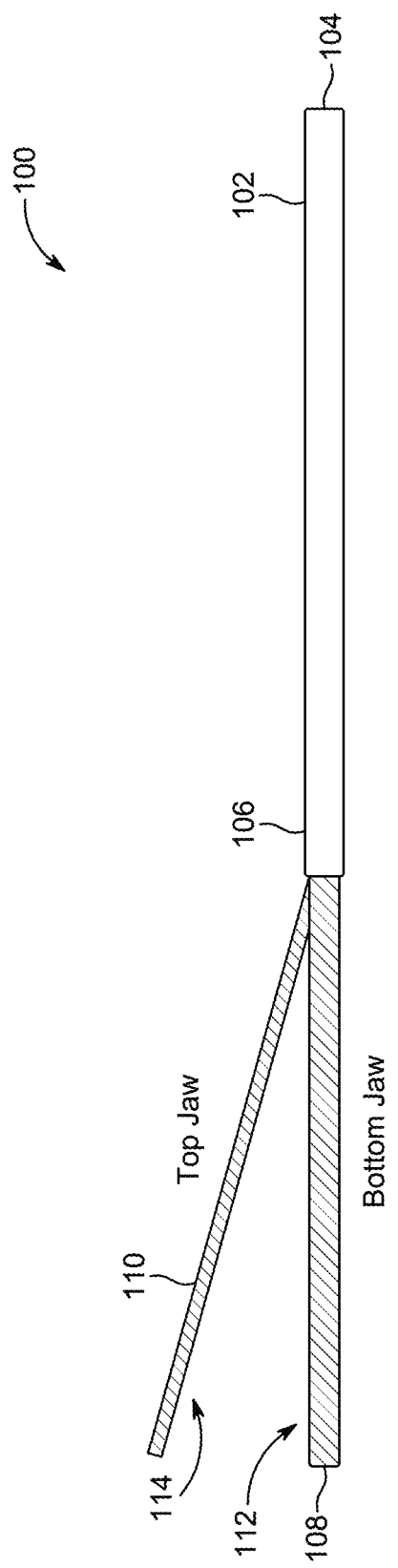
FIG. 1 illustrates a side view of a surgical stapler instrument, in accordance with a present embodiment.

FIG. 1 illustrates a side view of a surgical stapler instrument 100, in accordance with the present embodiment.

The surgical stapler instrument 100 is employed in invasive surgical procedures to cut and staple targeted tissue. The surgical stapler instrument 100 may include a handle assembly 102, having a proximal end 104 and a distal end 106. The handle assembly 102 is configured to maneuver the surgical stapler instrument 100 in multiple directions. Further, the surgical stapler instrument 100 may comprise a bottom jaw 108 and a top jaw 110. The bottom jaw 108 may be detachably coupled to the distal end 106 of the handle assembly 102. In one embodiment, the top jaw 110 may be detachably coupled to the bottom jaw 108 towards the distal end 106 of the handle assembly 102. It may be noted that the bottom jaw 108 and the top jaw 110 are the opposite jaws that are placed at each side of targeted tissue, such that the bottom jaw 108 and the top jaw 110 may contact with the targeted tissue that is to be treated.

Further, the bottom jaw 108 may include a staple cartridge surface 112 and a linear slider (not shown). The staple cartridge surface 112 is configured to house one or more surgical staples (not shown) that are to be used for closing or stapling wounds or surgical cuts. It may be noted that the one or more surgical staples may be placed along the length of the bottom jaw 108. In an embodiment, the one or more surgical staples may be constructed from material selected from a group of materials such as, but is not limited to, stainless steel, titanium, and plastic. In one exemplary embodiment, the one or more surgical staples made of plastic material are frequently used for patients with metal allergies or to reduce scar tissues. Further, the linear slider is configured to slide linearly over the staple cartridge surface 112, such that the one or more surgical staples placed inside the staple cartridge surface eject out from the bottom jaw 108 and insert into the targeted tissue or the body part that is to be treated.

Further, the top jaw 110 may comprise a staple pocket 114 disposed over an anvil surface (not shown). In one embodiment, the anvil surface may correspond to a flat surface to align the one or more surgical staples ejected from the staple cartridge surface 112. It may be noted that the top jaw 110 is placed in such a manner that the one or more surgical staples ejected from the bottom jaw 108 are received in alignment to the staple pocket 114. Further, the anvil surface may be used to compress and bend the one or more surgical staples once aligned to bind the targeted tissue that is to be treated.

Figure 2:
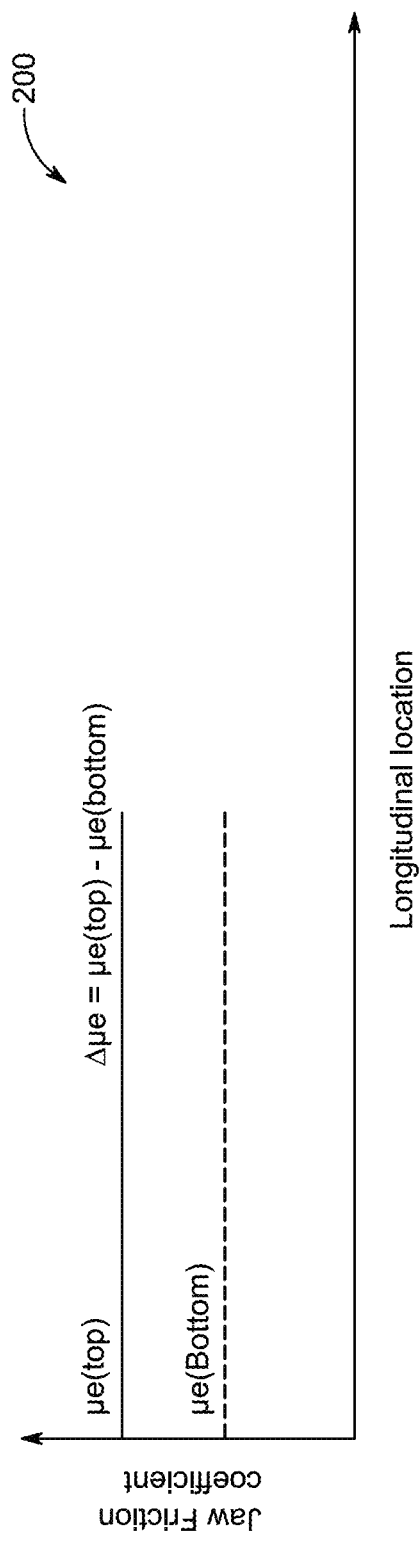
FIG. 2 illustrates a plot showing an effective friction coefficient difference of two opposing jaw surfaces of the surgical stapler instrument, in accordance with the present embodiment.

FIG. 2 illustrates a plot 200 showing an effective friction coefficient difference ($\Delta\mu e$) of two opposing jaw surfaces of the surgical stapler instrument 100, in accordance with the present embodiment.

Referring to FIG. 2, the plot 200 may be in between longitudinal location (x-axis) and jaw friction coefficient (y-axis). In an embodiment, the effective friction coefficient (μe) is represented by μe=Fnormal/Ffriction, where Fnormal is compression force, and Ffriction is friction force when pushed against the targeted tissue. It may be noted that the effective friction coefficient (μe) may be impacted by surface condition or even surface topological feature.

The effective friction coefficient (μe) of the bottom jaw 108 is represented as $μe_{(bottom)}$ and the effective friction coefficient (μe) of the top jaw 110 is represented as $μe_{(top)}$. The effective friction coefficient difference (Δμe) may be optimized along a length of the top jaw 110 and the bottom jaw 108. The plot 200 represents that $μe_{(top)}$ is higher than $μe_{(bottom)}$. Further, $μe_{(top)}$ and $μe_{(bottom)}$ varies linearly along the length of the top jaw 110 and the bottom jaw 108.

The effective friction coefficient difference (Δμe) may be referred to as delta of effective friction coefficient (μe) between the top jaw 110 and the bottom jaw 108. The effective friction coefficient difference (Δμe) may be calculated using a mathematical equation:

$$Δμe=μe(Top)-μe(Bottom).$$

It can be noted that the effective friction coefficient difference (Δμe) may be less than or equal to 0.25. The low effective friction coefficient difference (Δμe) enables the bottom jaw 108 and the top jaw 110 to move uniformly over the tissue surface and staple the one or more surgical staples on each side of the targeted tissue. The targeted tissue may also correspond to a target area. To achieve a uniform motion over the tissue surface, the top jaw 110 and the bottom jaw 108 may be treated to achieve a substantial similar effective friction performance.

In an alternate embodiment, the effective friction coefficient (μe) may be consistent throughout contacting length of the bottom jaw 108 and the top jaw 110. In another alternate embodiment, the effective friction coefficient (μe) may vary throughout contacting length of the bottom jaw 108 and the top jaw 110. The variation of the effective friction coefficient (μe) may depend on location or area on the bottom jaw 108 and the top jaw 110 and type of the surface treatment. It can be noted that the lateral force may be controlled for the targeted tissue effect, as long as the delta of the effective friction coefficient (μe) between the top jaw 110 and the bottom jaw 108 is less than or equal to 0.25.

Further, the staple cartridge surface 112 of the bottom jaw 108 may be constructed with higher effective friction coefficient (μe) than the staple pocket 114 of the top jaw 110 to facilitate optimized stapling. It can be noted that the top jaw 110 may be further optimized with staple pocket 114 is constructed with a lower effective friction coefficient (μe) than the anvil surface. The lower effective friction coefficient (μe) of the staple pocket 114 may achieve best staple formation with low friction force. Further, the anvil surface of the top jaw 110 may facilitate enhancement in manipulation of the targeted tissue. In one embodiment, the anvil surface may comprise a flat portion having a higher effective friction coefficient (μe) as compared to the staple pocket portion of the anvil surface.

In an embodiment, the bottom jaw 108 and the top jaw 110 may be optimized, such that the effective friction coefficient difference (Δμe) of two opposing jaw surface of the bottom jaw 108 and the top jaw 110 is substantially similar. In one embodiment, the bottom jaw 108 and the top jaw 110 may have a stainless-steel surface. The stainless-steel surface of the bottom jaw 108 and the top jaw 110 may be treated with biocompatible polymer coating, such as, but not limited to, Polyethylene glycol (PEG) and polydimethylsiloxane (PDMS). The treatment of the bottom jaw 108 and the top jaw 110 with biocompatible polymer will reduce tissue/metal surface friction. It can be noted that tissue/metal surface friction of the bottom jaw 108 and the top jaw 110 may be like tissue/plastic friction of the bottom jaw 108 and the top jaw 110. In one embodiment, a plastic surface of the bottom jaw 108 and the top jaw 110 may be treated with certain metallic coating using electroplating or Vacuum Metallizing. The metallic coating may be a material selected from a group of materials of aluminum, copper, and titanium. It can be noted that the plastic surface may be also oxidized to form ceramic coating to further tailor the friction coefficient.

Figure 3:
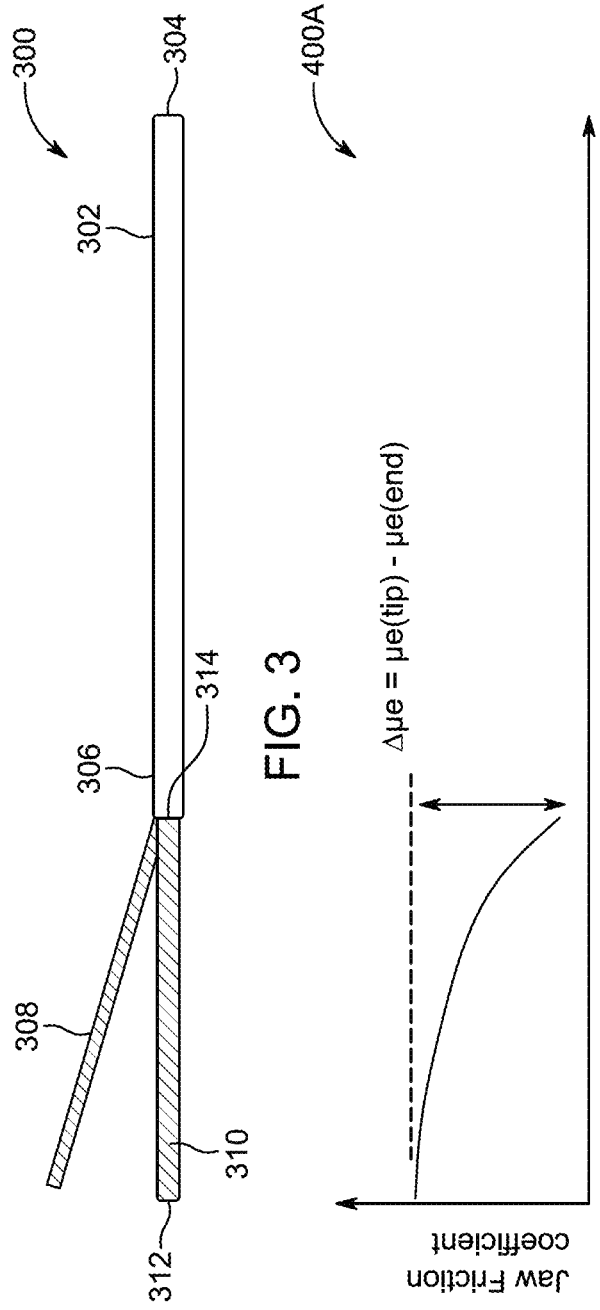
FIG. 3 illustrates a side view of a surface optimized surgical shear instrument, in accordance with the present embodiment.

FIG. 3 illustrates a side view of a surface optimized surgical shear instrument 300, in accordance with the present embodiment. FIG. 3 will be described in conjunction with FIGS. 4A and 4B.

The surface optimized surgical shear instrument 300 may also be referred to as a surgical shear instrument. The surface optimized surgical shear instrument 300 may be configured to allow a user to make precise osteotomies while protecting collateral or adjacent soft tissue structures. The surface optimized surgical shear instrument 300 may be used in various open and laparoscopic surgeries, tonsillectomy, dental and ophthalmic surgeries. The surface optimized surgical shear instrument 300 converts the ultrasonic energy into mechanical energy. The surface optimized surgical shear instrument 300 uses longitudinal ultrasonic vibrations to cut and coagulate tissue.

The surface optimized surgical shear instrument 300 comprises a handle assembly 302 having a proximal end 304 and a distal end 306. The handle assembly 302 may be configured to manipulate the surface optimized surgical shear instrument 300. Further, the surface optimized surgical shear instrument 300 may comprise a non-active jaw 308 and an ultrasonic blade 310. The ultrasonic blade 310 may be detachably coupled to the distal end 306 of the handle assembly 302, and the non-active jaw 308 may be detachably coupled to the ultrasonic blade 310 towards the distal end 306 of the handle assembly 302.

The non-active jaw 308 and the ultrasonic blade 310 may be placed at the opposite side of the targeted tissue that is to be treated. The ultrasonic blade 310 is configured to vibrate at a high frequency to generate a frictional heat that allows protein in the targeted tissues to denature into an adhesive material called coagulum and to seal the vessel. In one embodiment, the ultrasonic blade 310 oscillates between 20-50 Mega Hz, once placed in the targeted tissue to cause coagulation.

Further, the ultrasonic blade 310 comprises a distal tip section 312 and a proximal node section 314. The proximal node section 314 is positioned towards the distal end 306 of the handle assembly 302 and the distal tip section 312 corresponds to an extreme sharp point of the ultrasonic blade 310. In one embodiment, the distal tip section 312 is a leading section, and the proximal node section 314 is a trailing section of the ultrasonic blade 310. The ultrasonic blade 310 may be designed to vibrate as a free-standing wave configuration. In one embodiment, the distal tip section 312 of the ultrasonic blade 310 generally vibrates at highest displacement with minimal stress. Further, surface optimized surgical shear instrument 300 may close the non-active jaw 308, the vessel or the targeted tissue tends to flow towards the distal tip section 312 of the ultrasonic blade 310. It can be noted that the flow of the targeted tissue towards the distal tip section 312 of the ultrasonic blade 310 is achieved when the ultrasonic blade 310 is surface treated with a uniform surface friction in comparison to the non-active jaw 308. The uniform surface friction allows uniform movement of the ultrasonic blade 310.

Figure 4A:
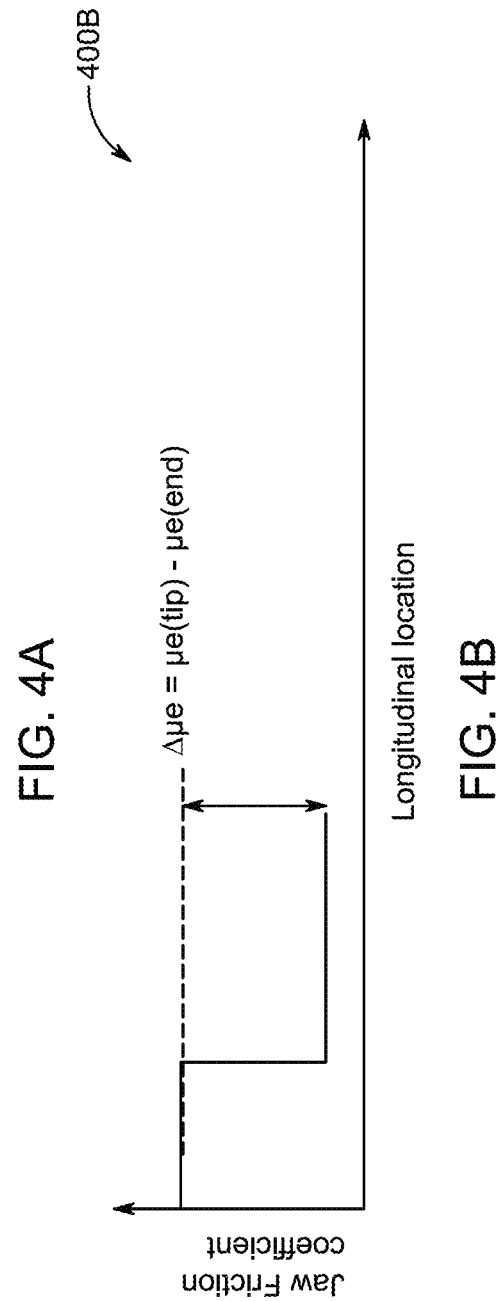
FIG. 4A illustrates a plot showing a gradual decay of the effective friction coefficient (μe) from a distal tip section to a proximal node section of an ultrasonic blade, in accordance with the present embodiment.
Figure 4B:
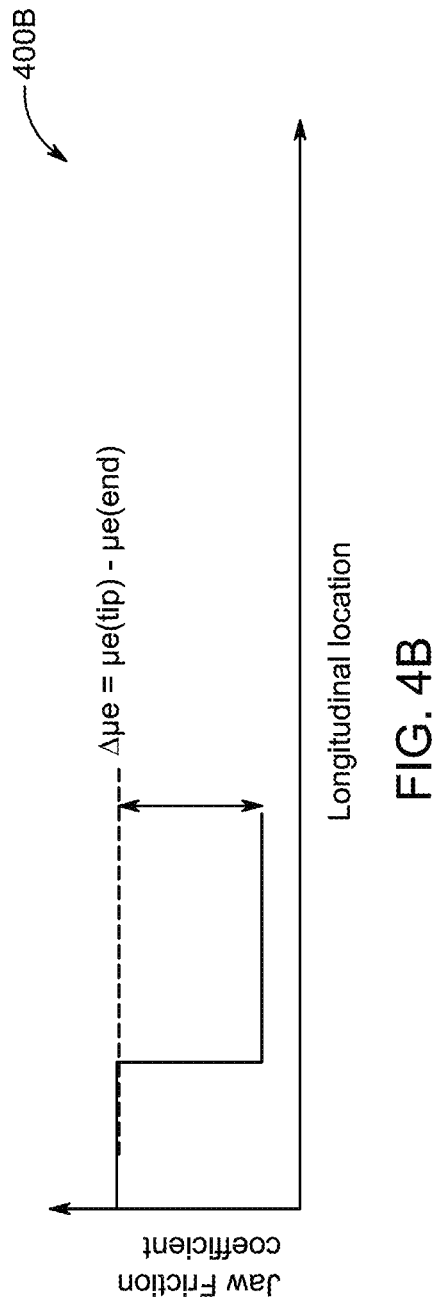
FIG. 4B illustrates a plot showing a step decay of the effective friction coefficient (μe) from the distal tip section to the proximal node section of the ultrasonic blade, in accordance with the present embodiment.

Referring to FIGS. 4A-4B, plots 400A and 400B, show a gradual decay and a step decay of the effective friction coefficient (µe) from the distal tip section 312 to the proximal node section 314 of the ultrasonic blade 310, in accordance with the present embodiment.

The effective friction coefficient (µe) of the ultrasonic blade 310 may have a descending order from the distal tip section 312 to the proximal node section 314. The effective friction coefficient (µe) may be highest at the distal tip section 312 and the effective friction coefficient (µe) may be lowest at the proximal node section 314. In one embodiment, the change of the effective friction coefficient (µe) between the distal tip section 312 and the proximal node section 314 may be gradually reduced, as shown by the plot 400A. In another embodiment, the change of the effective friction coefficient (µe) between the distal tip section 312 and the proximal node section 314 may have a step change, as shown by the plot 400B.

Further, the effective friction coefficient difference (Δµe) between the distal tip section 312 and the proximal node section 314 of the ultrasonic blade 310 may be equal to or larger than 0.1. The effective friction coefficient difference (Δµe) of 0.1 may facilitate a higher friction force at the distal tip section 312 of the ultrasonic blade 310 to retain the targeted tissue and the vessel. In one embodiment, the effective friction coefficient difference (Δµe) may be referred as an optimal delta or an optimal change of the effective friction coefficient (µe) between the distal tip section 312 and the proximal node section 314 of the ultrasonic blade. It can be noted that the effective friction coefficient difference (Δµe) between the distal tip section 312 and the proximal node section 314 may be achieved by the surface treatment. In one embodiment, the surface treatment may include, but not limited to, laser treatment, blasting, shot peening, or chemical reaction.

Figure 5:
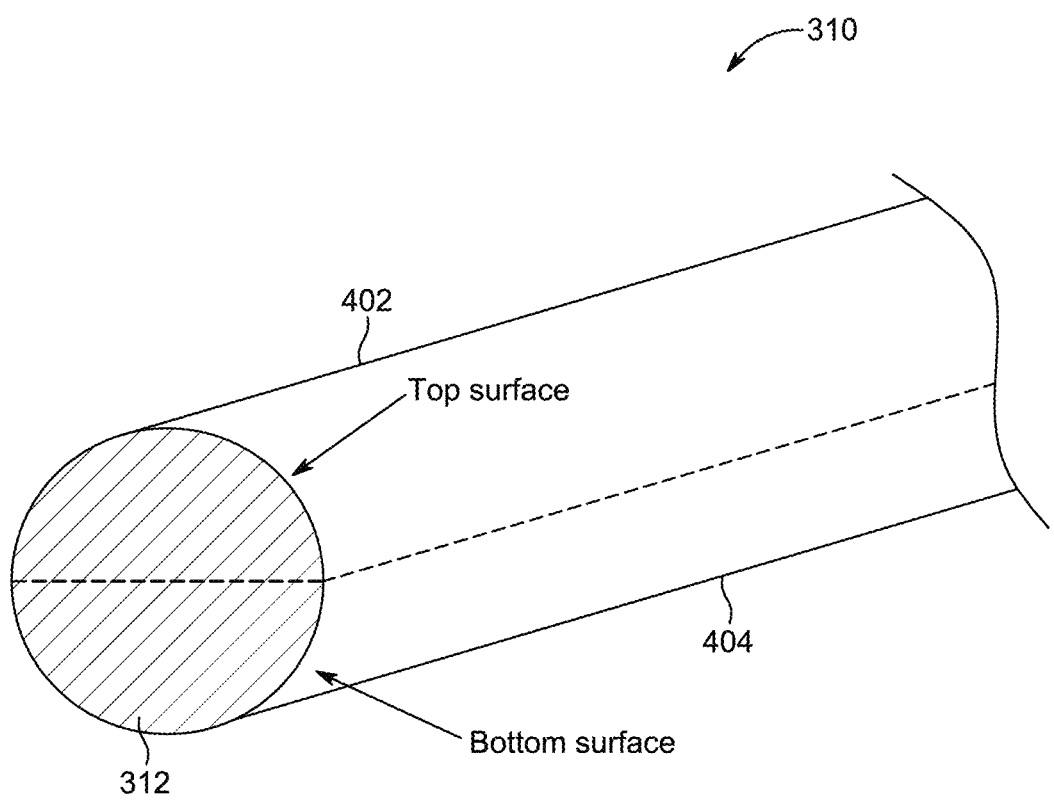
FIG. 5 illustrates a top surface and a bottom surface of the ultrasonic blade, in accordance with the present embodiment.

FIG. 5 illustrates a top surface 502 and a bottom surface 504 of the ultrasonic blade 310, in accordance with the present embodiment. In one embodiment, the top surface 502 and the bottom surface 504 of the ultrasonic blade 310 may be designed to have the effective surface friction coefficient (µe) uniformly distributed along the length of the top surface 502 and the bottom surface. According to another embodiment, the effective surface friction coefficient (µe) may vary depending on circumferential location of the ultrasonic blade 310. For instance, the top surface 502 of the ultrasonic blade 310, is an opposing surface of the non-active jaw 308, is fabricated with a higher frictional surface, and the bottom surface 504 of the ultrasonic blade 310 is fabricated with a lower frictional surface. In one embodiment, the effective friction coefficient (µe) of the top surface 502 may be higher than the bottom surface 504 of the ultrasonic blade 310.

In one embodiment, the non-active jaw 308 and the ultrasonic blade 310 of the surface optimized surgical shear instrument 300 may be optimized, such that the effective friction coefficient difference (Δµe) of the non-active jaw 308 and the ultrasonic blade 310 is substantially similar. In another embodiment, the non-active jaw 308 may be treated with the metal surface, such as, stainless steel and the ultrasonic blade 310 may be treated with biocompatible polymer coating, such as, Polyethylene glycol (PEG) and polydimethylsiloxane (PDMS). It can be noted that the treatment of the non-active jaw 308 and the ultrasonic blade 310 may reduce the targeted tissue/metal surface friction. In one exemplary case, the non-active jaw 308 and the ultrasonic blade 310 may have a plastic surface. In this case, the non-active jaw 308 and the ultrasonic blade 310 may be treated with certain metallic coating using electroplating or Vacuum Metallizing. In another exemplary case, the non-active jaw 308 and the ultrasonic blade 310 may have a metallic coating. The metallic coating may be selected from a group of materials of Al, Cu, and Ti. It can be noted that the plastic surface of the active jaw 308 and the ultrasonic blade 310 may be oxidized to form a ceramic coating to further tailor the effective friction coefficient (µe).

In one embodiment, the non-active jaw 308 may comprise a jaw surface (not shown) with varying surface friction. The jaw surface may have a change in surface friction coefficient between the distal tip section 312 and the proximal node section 314. In one exemplary embodiment, the change in the surface friction coefficient is greater or equal to 0.1.

Referring to FIG. 6A-6E, the different surface modifications of the ultrasonic blade 310 may be achieved using different surface treatments, in accordance with the present embodiment.

In an embodiment, the ultrasonic blade 310 may be treated with the metal surface and may be etched by a solution or a laser treatment to achieve a desired surface texture. For example, superhydrophobic surfaces, with steady contact angle of approximately 154° and contact angle hysteresis of approximately 4°, may be fabricated using a direct laser texturing. The direct laser texturing is a low waste, single-step procedure with potentially high processing rate. The direct laser texturing may control surface roughness or wettability directly on the metal surface of the ultrasonic blade 310 without coating. In an embodiment, the direct laser texturing may achieve different surface modification, such as, parallel lines finish 602, perpendicular lines finish 604, a micro grid finish 606, micro spots finish 608 and an anodized surface finish 610, as shown in FIGS. 6A-6E. In an embodiment, the parallel lines finish 602, the perpendicular lines finish 604, the micro grid finish 606, the micro spots finish 608 and the anodized surface finish 610, may correspond microscopic lines fabricated over the top surface 502 and the bottom surface 504 of the ultrasonic blade 310.

Figure 6A:
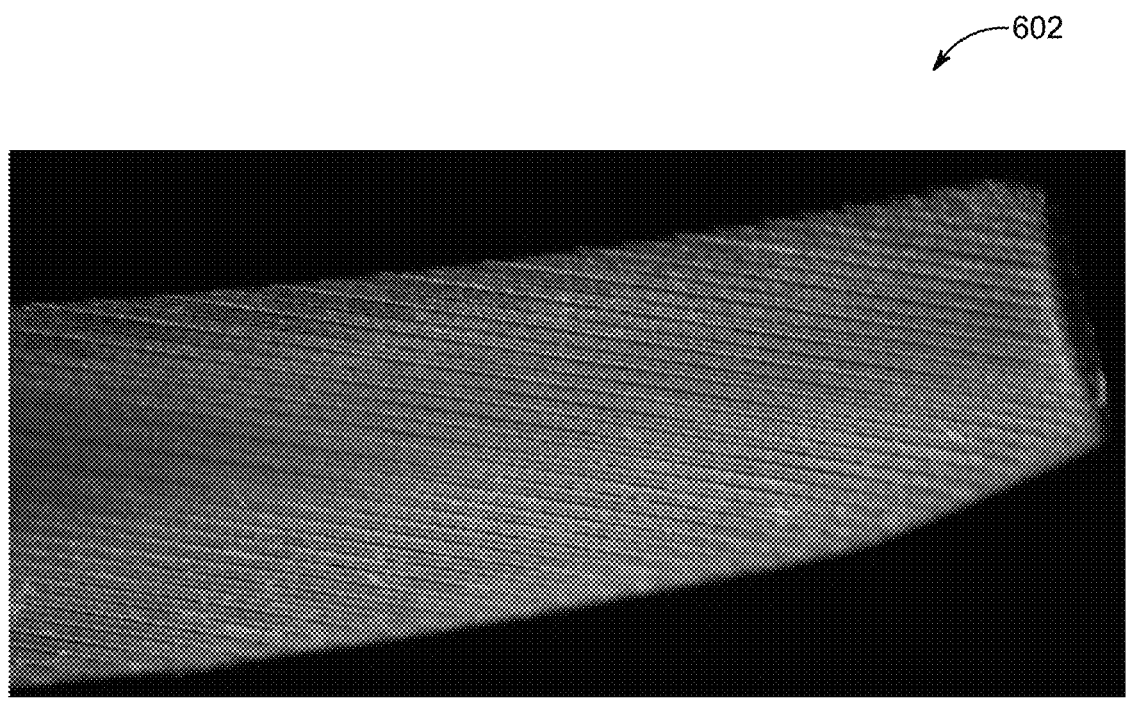
FIGS. 6A-6E illustrate surface modifications of the ultrasonic blade using different surface treatments, in accordance with the present embodiment.

FIG. 6A illustrates the parallel lines finish 602 of the ultrasonic blade 310 with a fixed hatch distance. The microscopic lines are parallel to the movement of the surface optimized surgical shear instrument 300 over the targeted tissue while treating the patient. It can be noted that the parallel lines finish 602 allows to reduce the effective surface friction coefficient (µe) of the ultrasonic blade 310. In one case, when the movement of the surface optimized surgical shear instrument 300 is in forward and/or backward direction, the effective surface friction coefficient (µe) is reduced. In another case, when the movement of the surface optimized surgical shear instrument 300 is in a lateral direction, the effective surface friction coefficient (µe) is increased.

Figure 6B:
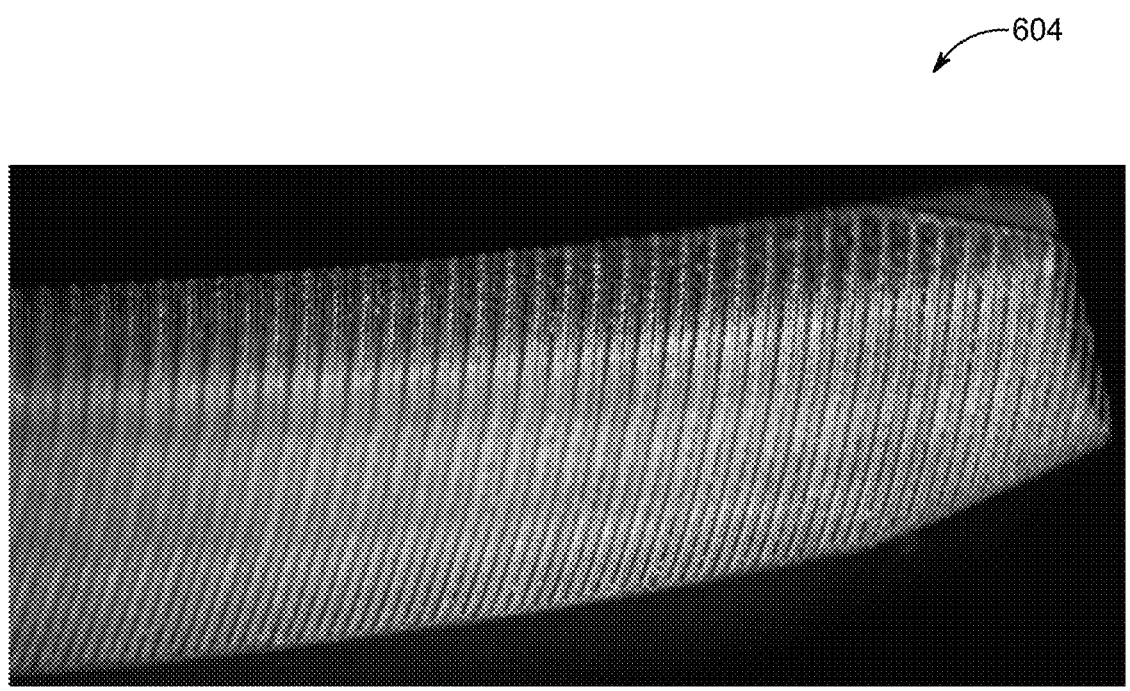

FIG. 6B illustrates the perpendicular lines finish 604 over the ultrasonic blade 310. In an embodiment, the microscopic lines fabricated over the surface of the ultrasonic blade 310 are perpendicular to the movement of the of the surface optimized surgical shear instrument 300 over the targeted tissue while treating the patient. In case of the perpendicular lines finish 604, the microscopic lines resist the movement of the surface optimized surgical shear instrument 300 and thereby the effective surface friction coefficient (µe) of the ultrasonic blade 310 increases drastically. In one case, when the movement of the surface optimized surgical shear instrument 300 is in forward and/or backward direction, the effective surface friction coefficient (µe) increases. In another case, when the movement of the surface optimized surgical shear instrument 300 is in lateral direction, the effective surface friction coefficient (µe) decreases.

Figure 6C:
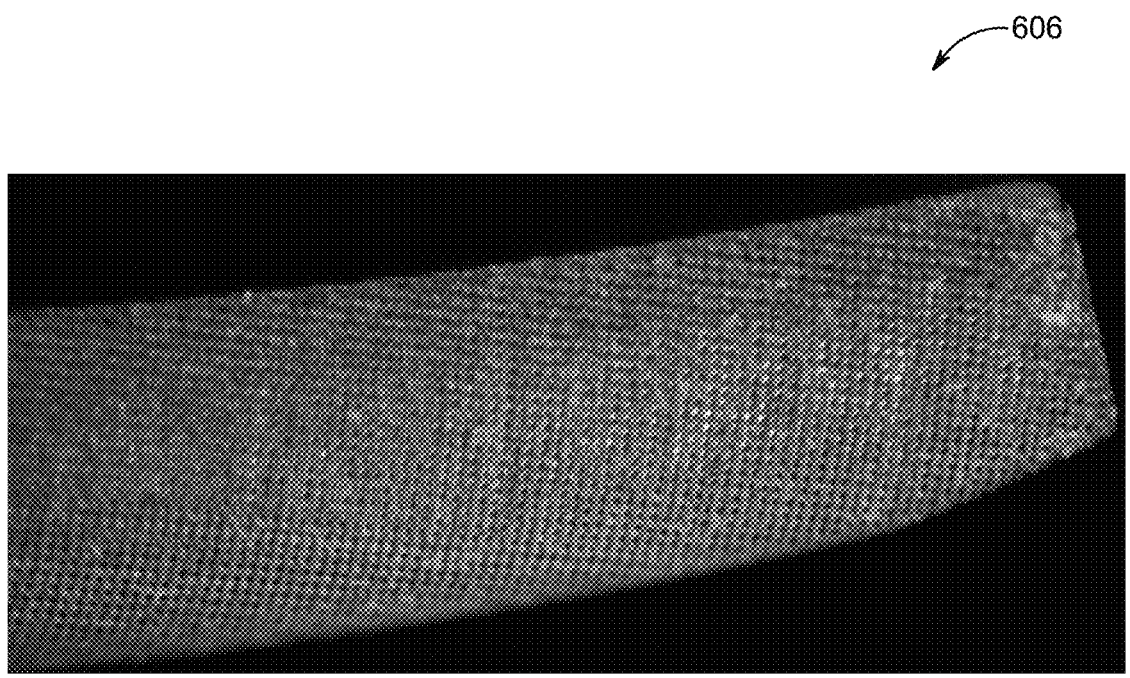

FIG. 6C illustrates the micro grid finish 606 over the ultrasonic blade 310. In an embodiment, the microscopic lines are fabricated over the surface of the ultrasonic blade 310 in a grid pattern or crisscross pattern. The grid pattern of the top surface 502 and the bottom surface 504 of the ultrasonic blade 310 allows to reduce the effective surface friction coefficient (µe) in both forward and/or backward direction movement, and lateral direction movement.

Figure 6D:
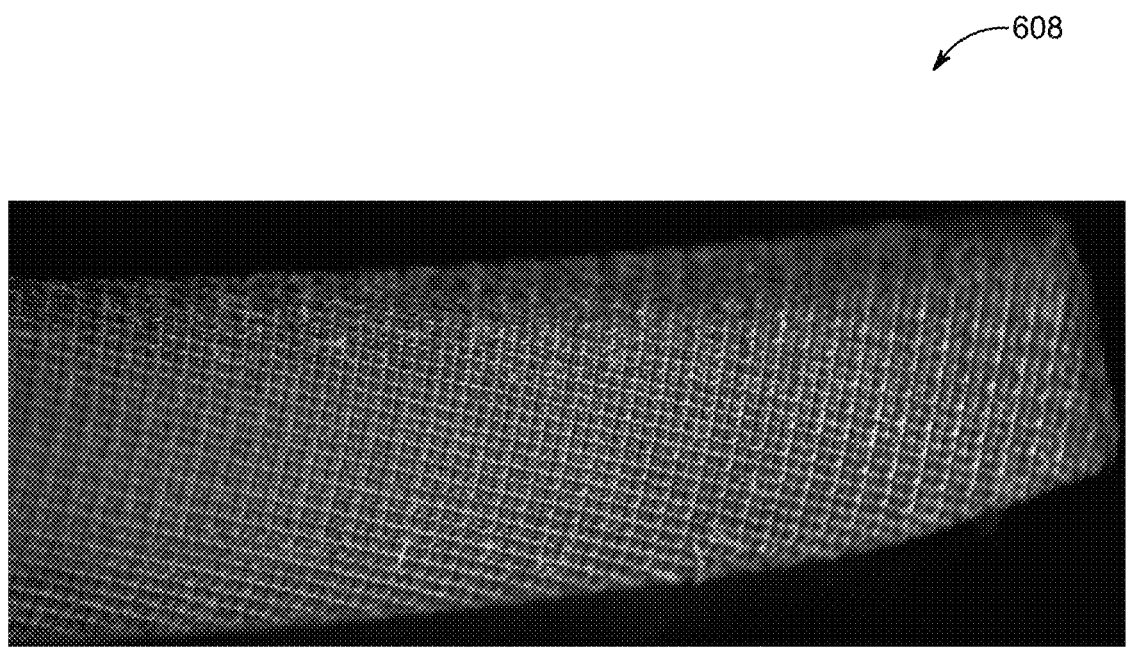

FIG. 6D illustrates the micro spots finish 608 over the ultrasonic blade 310. In an embodiment, the top surface 502 and the bottom surface 504 of the ultrasonic blade 310 may also be fabricated with a plurality of circular shaped spots (not shown).

Figure 6E:
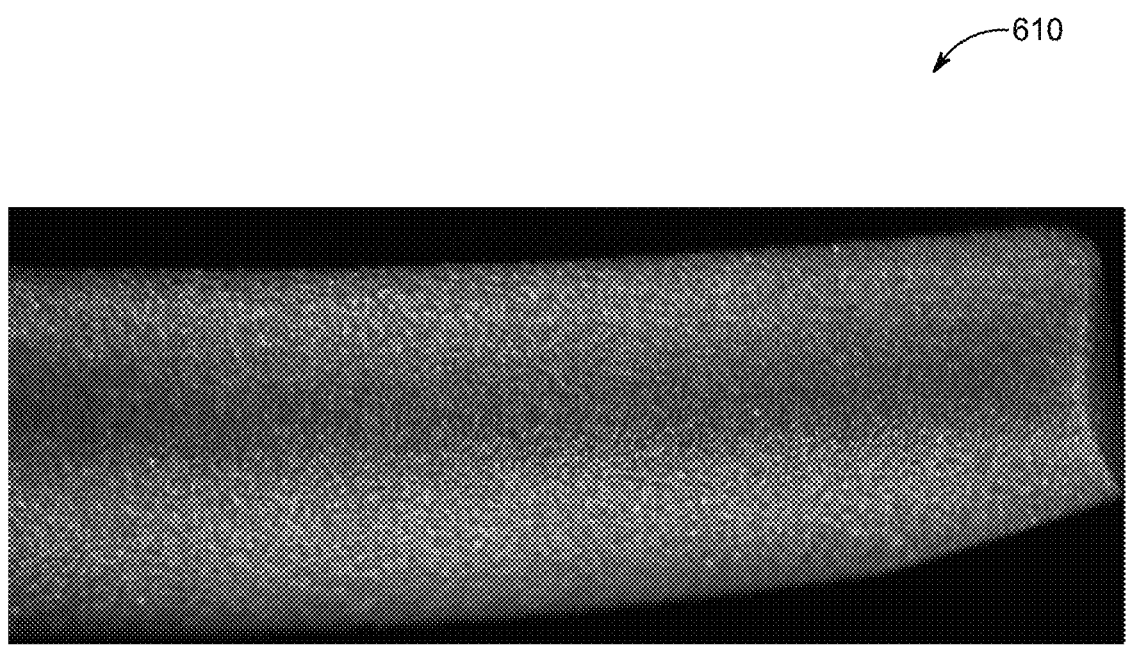

FIG. 6E illustrates the anodized surface finish 610 over the ultrasonic blade 310. It may be noted that the micro spots finish and the anodized surface finish may be used for different types of cutting operations, such as, a back cutting operation, a front cutting operation, a to cut soft tissues etc. In case of the back cutting operations, the top surface 502 may have lower friction surface, and the bottom surface 504 may have higher friction surface. In one alternate exemplary embodiment, surgical instruments having two opposite jaws may be surface finished to alter the effective surface friction coefficient (µe). For example, the surgical instruments include, an ultrasonic shear, a bipolar shear, and other energized forceps.

The features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Features that are described and/or illustrated with respect to one embodiment may be used in the same way or in a similar way in one or more other embodiments and/or in combination with or instead of the features of the other embodiments.

While the preferred embodiment of the present invention has been illustrated and described, as noted above, many changes can be made without departing from the spirit and scope of the invention. For example, aspects of the present invention may be adopted on alternative operating systems. Accordingly, the scope of the invention is not limited by the disclosure of the preferred embodiment. Instead, the invention should be determined entirely by reference to the claims that follow.

LIST OF ELEMENTS

Surgical Instruments

100 Surgical Stapler Instrument
102 Handle assembly
104 Proximal End
106 Distal End
108 Bottom Jaw
110 Top Jaw
112 Staple Cartridge Surface
114 Staple Pocket
200 Plot
300 Surface Optimized Surgical Shear Instrument
302 Handle Assembly
304 Proximal End
306 Distal End
308 Non-Active Jaw
310 Ultrasonic Blade
312 Distal Tip Section
314 Proximal Node Section
400A Plot
400B Plot
502 Top Surface
504 Bottom Surface
602 Parallel Lines Finish
604 Perpendicular Lines Finish
606 Micro Grid Finish
608 Micro Spot Finish
610 Anodized Surface Finish

What is claimed is:

1. A surface optimized surgical shear instrument, comprising:
   a handle assembly having a proximal end and a distal end;
   an ultrasonic blade detachably coupled to the distal end of the handle assembly; and
   a non-active jaw detachably coupled to the ultrasonic blade towards the distal end of the handle assembly,
   wherein the ultrasonic blade is configured to vibrate at high frequency with an effective friction coefficient varying from a distal tip section to a proximal node section, wherein the effective friction coefficient of the distal tip section is higher than the proximal node section of the ultrasonic blade.

2. The surface optimized surgical shear instrument of claim 1, wherein the ultrasonic blade having a top surface and a bottom surface, wherein the effective friction coefficient (µe) of the top surface is greater than the effective friction coefficient (µe) of the bottom surface to retain a tissue and vessel during a surgery.

3. The surface optimized surgical shear instrument of claim 2, wherein the effective friction coefficient (µe) of the top surface and the bottom surface is reversible in case of executing blade back cutting operation.

4. The surface optimized surgical shear instrument of claim 1, wherein a change in surface friction coefficient along a length of the ultrasonic blade, between the distal tip section and the proximal node section, is greater or equal to 0.1.

5. The surface optimized surgical shear instrument of claim 4, wherein the change in the surface friction coefficient along the length of the ultrasonic blade is achieved by a surface treatment between the distal tip section and the proximal node section.

6. The surface optimized surgical shear instrument of claim 1, wherein the opposing non-active jaw has a change in surface friction coefficient along a jaw surface between the distal tip section and the proximal node section, wherein the change in the surface friction coefficient is greater or equal to 0.1.

* * * * *